(12) United States Patent
Lee

(10) Patent No.: US 9,527,508 B1
(45) Date of Patent: Dec. 27, 2016

(54) MOBILE VEHICLE SAFETY APPARATUS AND SAFETY MONITORING METHOD THEREOF

(71) Applicant: Winbond Electronics Corp., Taichung (TW)

(72) Inventor: Chen-Yi Lee, Hsinchu (TW)

(73) Assignee: Winbond Electronics Corp., Taichung (TW)

(*) Notice: Subject to any disclaimer, the term of this patent is extended or adjusted under 35 U.S.C. 154(b) by 0 days.

(21) Appl. No.: 14/873,168

(22) Filed: Oct. 1, 2015

(30) Foreign Application Priority Data

Aug. 13, 2015 (CN) .......................... 2015 1 0495642

(51) Int. Cl.

| | |
|---|---|
| *A61B 5/04* | (2006.01) |
| *B60W 30/08* | (2012.01) |
| *B60W 40/08* | (2012.01) |
| *A61B 5/0408* | (2006.01) |
| *A61B 5/00* | (2006.01) |
| *A61B 5/0432* | (2006.01) |
| *A61B 5/18* | (2006.01) |
| *A61B 5/11* | (2006.01) |

(52) U.S. Cl.
CPC ............ *B60W 30/08* (2013.01); *A61B 5/0408* (2013.01); *A61B 5/04012* (2013.01); *A61B 5/0432* (2013.01); *A61B 5/1114* (2013.01); *A61B 5/18* (2013.01); *A61B 5/6893* (2013.01); *A61B 5/742* (2013.01); *A61B 5/7405* (2013.01); *A61B 5/746* (2013.01); *B60W 40/08* (2013.01); *B60W 2040/0818* (2013.01); *B60W 2540/26* (2013.01); *B60W 2720/10* (2013.01); *B60W 2900/00* (2013.01)

(58) Field of Classification Search
None
See application file for complete search history.

(56) References Cited

U.S. PATENT DOCUMENTS

| 4,569,536 A | 2/1986 | Tsuge et al. |
| 6,104,296 A * | 8/2000 | Yasushi .............. A61B 5/04085 |
| | | 180/272 |
| 6,575,902 B1 * | 6/2003 | Burton ..................... A61B 5/18 |
| | | 340/575 |

(Continued)

FOREIGN PATENT DOCUMENTS

| TW | 200629182 | 8/2006 |
| TW | 200906361 | 2/2009 |

(Continued)

OTHER PUBLICATIONS

"Office Action of Taiwan Counterpart Application", issued on Feb. 25, 2016, p. 1-p. 6, in which the listed references were cited.

(Continued)

*Primary Examiner* — Jonathan M Dager
(74) *Attorney, Agent, or Firm* — Jianq Chyun IP Office

(57) ABSTRACT

A mobile vehicle safety apparatus and a safety monitoring method thereof are provided. The safety monitoring method is as follows. A physiological status of a driver is determined according to an electrocardiogram signal and electrocardiogram history data, and the mobile vehicle is driven according to the physiological status of the driver.

8 Claims, 4 Drawing Sheets

(56) References Cited

U.S. PATENT DOCUMENTS

| | | | | |
|---|---|---|---|---|
| 7,605,694 B2* | 10/2009 | Prost-Fin | ............... | B60K 35/00 340/438 |
| 8,684,938 B2* | 4/2014 | Sakai | ................... | A61B 5/4035 600/481 |
| 8,698,639 B2* | 4/2014 | Fung | ...................... | B60K 28/06 340/576 |
| 8,870,782 B2* | 10/2014 | Futatsuyama | ...... | A61B 5/02125 600/485 |
| 9,144,389 B2* | 9/2015 | Srinivasan | ........... | A61B 5/0408 |
| 9,292,471 B2* | 3/2016 | Fung | ..................... | B60W 40/09 |
| 2003/0073886 A1* | 4/2003 | Yanagidaira | ............. | A61B 5/18 600/300 |
| 2003/0097047 A1* | 5/2003 | Woltermann | .......... | A61B 5/165 600/300 |
| 2007/0265540 A1* | 11/2007 | Fuwamoto | ......... | A61B 5/04525 600/515 |
| 2010/0049068 A1* | 2/2010 | Fuwamoto | ........... | A61B 5/0408 600/509 |
| 2010/0137702 A1* | 6/2010 | Park | ..................... | A61B 5/0402 600/393 |
| 2011/0043350 A1* | 2/2011 | Ben David | ............. | B60Q 9/00 340/441 |
| 2012/0101690 A1 | 4/2012 | Srinivasan et al. | | |
| 2012/0179008 A1 | 7/2012 | Burton | | |
| 2012/0212353 A1* | 8/2012 | Fung | ...................... | B60K 28/06 340/905 |
| 2015/0258995 A1* | 9/2015 | Essers | .................... | G08G 1/163 340/576 |
| 2016/0009295 A1* | 1/2016 | Chun | .................... | A61B 5/6893 701/32.9 |
| 2016/0023666 A1* | 1/2016 | Lee | ....................... | B60W 50/14 701/33.4 |
| 2016/0272214 A1* | 9/2016 | Chen | ..................... | B60W 50/14 |

FOREIGN PATENT DOCUMENTS

| | | |
|---|---|---|
| TW | M444954 | 1/2013 |
| TW | 201328667 | 7/2013 |

OTHER PUBLICATIONS

Office Action of Taiwan Counterpart Application, issued on Sep. 26, 2016, p. 1-p. 6, in which the listed references were cited.

* cited by examiner

ID_VEHICLE SAFETY APPARATUS
AND SAFETY MONITORING METHOD
THEREOF

CROSS-REFERENCE TO RELATED
APPLICATION

This application claims the priority benefit of Chinese application serial no. 201510495642.8, filed on Aug. 13, 2015. The entirety of the above-mentioned patent application is hereby incorporated by reference herein and made a part of this specification.

BACKGROUND OF THE INVENTION

Field of the Invention

The invention relates to a safety apparatus, and particularly relates to a mobile vehicle safety apparatus and a safety monitoring method thereof.

Description of Related Art

Along with development of technology, safety requirements of mobile vehicles such as cars, motorcycles, etc., become higher and higher. In conventional techniques, cars and motorcycles are gradually equipped with a plurality of active or passive safety apparatuses, for example, a traction slip control system, an automatic tire pressure detection system, airbags, etc., and status detection of the mobile vehicle becomes more complete. However, driving safety is not completely decided by the status of the mobile vehicle, but is further related to a physiological status of a driver, and if the driver improperly drives the mobile vehicle due to doze off or physical discomfort, etc., a traffic accident is probably occurred to cause casualties.

SUMMARY OF THE INVENTION

The invention is directed to a mobile vehicle safety apparatus and a safety monitoring method thereof, by which driving safety of a mobile vehicle is greatly improved.

The invention provides a mobile vehicle safety apparatus. The mobile vehicle safety apparatus includes an electrode unit, an electrocardiogram signal generating unit, a storage unit, a driving unit and a control unit. The electrode unit is disposed on a direction control grip of a mobile vehicle, and is configured to receive an electric signal from a skin surface of a driver when the driver holds the direction control grip. The electrocardiogram signal generating unit is coupled to the electrode unit, and converts the electric signal to generate an electrocardiogram signal. The storage unit is coupled to the electrocardiogram signal generating unit, and stores electrocardiogram history data of the driver. The driving unit drives the mobile vehicle to move. The control unit is coupled to the electrocardiogram signal generating unit, the storage unit and the driving unit, and determines a physiological status of the driver according to the electrocardiogram signal and the electrocardiogram history data, and controls the driving unit to drive the mobile vehicle according to the physiological status of the driver.

In an embodiment of the invention, the control unit further determines whether to activate the driving unit according to the physiological status of the driver, and controls the driving unit to adjust a moving speed of the mobile vehicle according to the physiological status of the driver.

In an embodiment of the invention, the mobile vehicle safety apparatus further includes a video audio playing unit. The video audio playing unit is coupled to the control unit, and the control unit further determines a mental status of the driver according to the electrocardiogram signal, and controls the video audio playing unit to perform video audio playing according to at least one of the mental status and the physiological status of the driver.

In an embodiment of the invention, the storage unit further stores a plurality of predetermined video audio databases corresponding to a plurality of predetermined mental statuses, and the control unit controls the video audio playing unit to play content of the corresponding video audio database according to the predetermined mental status corresponding to the driver.

In an embodiment of the invention, the control unit further determines whether hands of the driver move away from the direction control grip according to the electrocardiogram signal, and the control unit controls the video audio playing unit to play a warning message when the hands of the driver move away from the direction control grip.

The invention provides a safety monitoring method for a mobile vehicle safety apparatus, which includes following steps. An electric signal is received from a skin surface of a driver through an electrode unit on a direction control grip of a mobile vehicle. The electric signal is converted to generate an electrocardiogram signal. A physiological status of the driver is determined according to the electrocardiogram signal and electrocardiogram history data. The mobile vehicle is driven according to the physiological status of the driver.

In an embodiment of the invention, the step of driving the mobile vehicle according to the physiological status of the driver includes following steps. It is determined whether to activate the mobile vehicle according to the physiological status of the driver, and a moving speed of the mobile vehicle is adjusted according to the physiological status of the driver.

In an embodiment of the invention, the safety monitoring method for the safety apparatus of the mobile vehicle further includes following steps. A mental status of the driver is determined according to the electrocardiogram signal. Video audio playing is performed according to at least one of the mental status and the physiological status of the driver.

In an embodiment of the invention, the step of performing video audio playing according to at least one of the mental status and the physiological status of the driver includes following steps. A predetermined mental status corresponding to the mental status of the driver is determined. Content of the corresponding video audio database is played according to the predetermined mental status corresponding to the driver.

In an embodiment of the invention, the safety monitoring method for the safety apparatus of the mobile vehicle further includes following steps. It is determined whether hands of the driver move away from the direction control grip. A warning message is played when the hands of the driver move away from the direction control grip.

According to the above descriptions, in the embodiment of the invention, the physiological status of the driver is determined according to the electrocardiogram signal and the electrocardiogram history data, and the driving unit is controlled to driver the mobile vehicle according to the physiological status of the driver, so as to greatly improve driving safety of the mobile vehicle.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated

DESCRIPTION OF EMBODIMENTS

Figure 1:
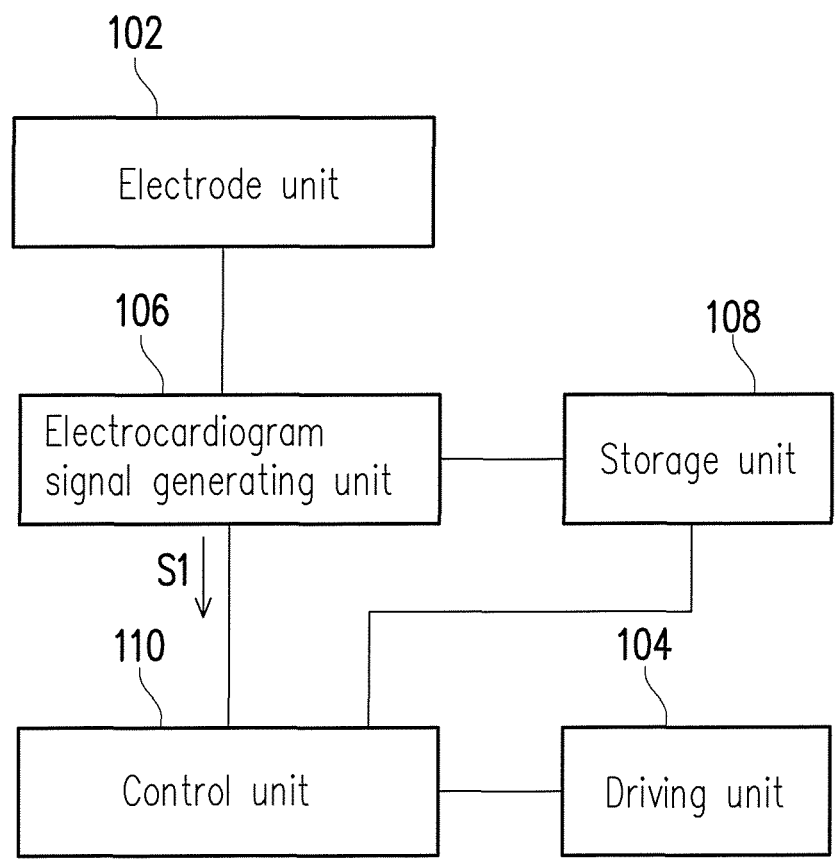
FIG. 1 is a schematic diagram of a mobile vehicle safety apparatus according to an embodiment of the invention.

FIG. 1 is a schematic diagram of a mobile vehicle safety apparatus according to an embodiment of the invention. Referring to FIG. 1, the mobile vehicle safety apparatus 100 includes an electrode unit 102, a driving unit 104, an electrocardiogram signal generating unit 106, a storage unit 108 and a control unit 110. The electrocardiogram signal generating unit 106 is coupled to the electrode unit 102 and the storage unit 108, and the control unit 110 is coupled to the driving unit 104, the electrocardiogram signal generating unit 106 and the storage unit 108. The electrode unit 102 can be disposed on a direction control grip of a mobile vehicle, for example, a steering wheel of a car or motorcycle grips, and is configured to receive an electric signal from a skin surface of a driver when the driver holds the direction control grip. The electrode unit 102, for example, includes two electrode patches, though the invention is not limited thereto. The electrocardiogram signal generating unit 106 may convert the electric signal into an electrocardiogram signal S1. The storage unit 108 may storage electrocardiogram history data of the user (i.e. the driver of the mobile vehicle) of the mobile vehicle safety apparatus 100. The control unit 110 may determine a physiological status of the driver according to the electrocardiogram signal S1 and the electrocardiogram history data, and control the driving unit 104 to drive the mobile vehicle according to the physiological status of the driver.

For example, when the mobile vehicle is not in a moving status, the control unit 110 determines whether to activate the driving unit 104 according to the physiological status of the driver, and if the control unit 110 determines that the physiological status of the driver is not suitable for driving the mobile vehicle, the control unit 110 does not activate the driving unit 104, so as to avoid a driving accident caused by physical discomfort of the driver. Moreover, if the mobile vehicle is already in the moving status, the control unit 110 may control the driving unit 104 to adjust a moving speed of the mobile vehicle according to the physiological status of the driver. For example, when the physiological status of the driver is not good, or the driver is too tired, the control unit 110 may control the control unit 104 to decrease the moving speed of the mobile vehicle, or decrease the maximum speed limit of the mobile vehicle.

The aforementioned electrocardiogram history data is, for example, electrocardiogram signal data of the driver stored in the storage unit 108 when the driver drives the mobile vehicle last time or before, for example, data of the electrocardiogram signal S1 stored when the driver drives the mobile vehicle last time. Alternatively, the storage unit 108 may store electrocardiogram signal data within a predetermined period as the electrode unit 102 starts to receive the electric signals when the driver drives the mobile vehicle for the first time, and takes the electrocardiogram signal data as the electrocardiogram history data. In this way, by determining the physiological status of the driver according to the electrocardiogram signal S1 and the electrocardiogram history data, and controlling the driving unit 104 to drive the mobile vehicle, driving safety of the mobile vehicle is greatly improved.

Moreover, the control unit 110 may analyze activities of a sympathetic nerve and a parasympathetic nerve of the driver according to the electrocardiogram signal S1, so as to determine a current mental status of the driver, and accordingly controls the driving unit 104 to adjust the moving speed of the mobile vehicle. For example, when the control unit 110 determines that the mental status of the driver is too excited according to the electrocardiogram signal S1, the control unit 110 may control the driving unit 104 to decrease the moving speed of the mobile vehicle, or decrease the maximum speed limit of the mobile vehicle, so as to decrease a chance of the car accident. It should be noted that besides that the electrocardiogram signal S1 is used for determining the mental status of the driver, it may include a plurality of physiological status information of the driver, for example, a heart rate, a heartbeat strength, a heart rate variability, etc., which can all be used as a reference for adjusting the moving speed of the mobile vehicle without being limited to the mental status of the driver.

Figure 2:
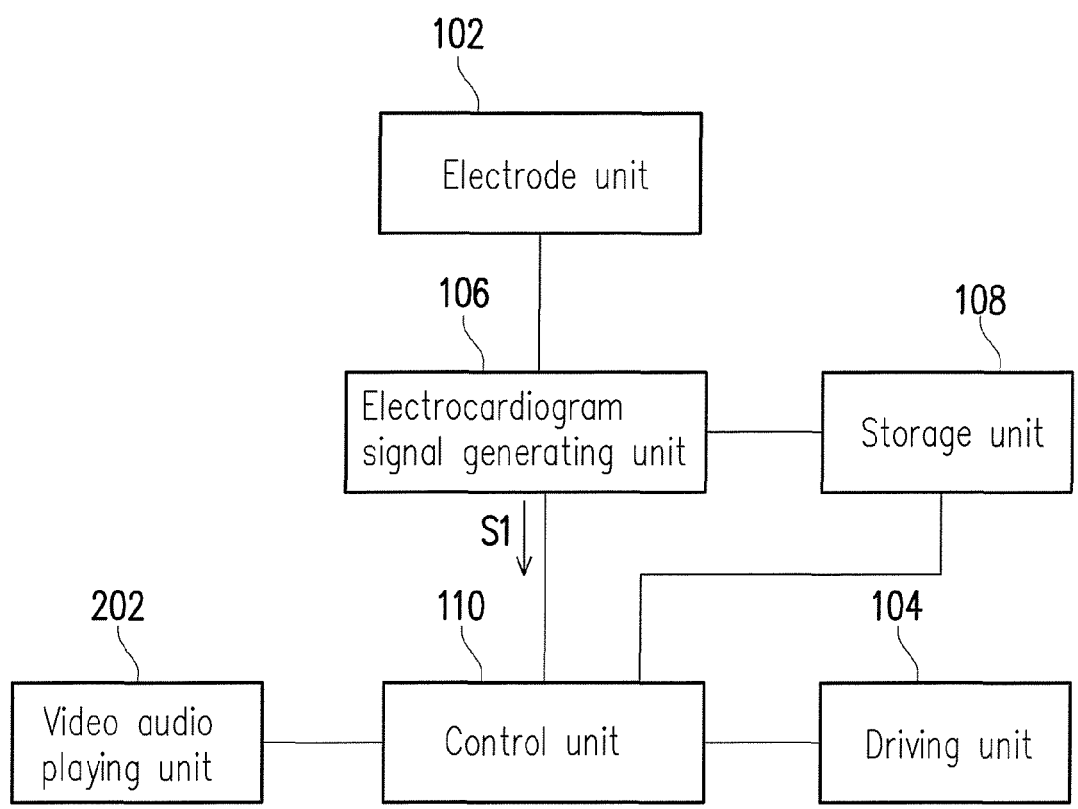
FIG. 2 is a schematic diagram of a mobile vehicle safety apparatus according to another embodiment of the invention.

FIG. 2 is a schematic diagram of a mobile vehicle safety apparatus according to another embodiment of the invention. Referring to FIG. 2, in the present embodiment, the mobile vehicle safety apparatus 200 further includes a video audio playing unit 202 coupled to the control unit 110. The video audio playing unit 202 is, for example, a liquid crystal display (LCD) or other device capable of playing video audio signals. In the present embodiment, the control unit 110 may determine the current mental status of the driver according to the electrocardiogram signal S1, and controls the video audio playing unit 202 to perform video audio playing according to at least one of the mental status and the physiological status of the driver. For example, when the control unit 110 determines that the driver is too tired according to the electrocardiogram signal S1, the control unit 110 may control the video audio playing unit 202 to play noisy video audio content to boost the spirit of the driver. Alternatively, when the control unit 110 determines that the nerve of the driver is too excited or nervous according to the electrocardiogram signal S1, the control unit 110 may control the video audio playing unit 202 to play relaxed video audio content to ease a nerve tension of the driver, so as to improve the driving safety of the mobile vehicle. In some embodiments, the storage unit 108 may store a plurality of predetermined video audio databases corresponding to a plurality of predetermined mental statuses, where the predetermined mental statuses are, for example, excited, nervous, relaxed, depressed, irritable, stable, etc., and the control unit may control to play content of the corresponding video audio database according to the predetermined mental status complied with the mental status of the driver, so as to make the mental status of the driver to be more suitable for driving the mobile vehicle and accordingly improve the driving safety of the mobile vehicle.

Moreover, during a process of measuring the electrocardiogram signal S1, both hands of the driver have to put on the direction control grip in order to effectively measure the electrocardiogram signal S1. Therefore, the control unit 110 may determine whether the hands of the driver move away from the direction control grip according to the electrocardiogram signal S1, and if the hands of the driver move away from the direction control grip, the control unit 110 cannot receive the electrocardiogram signal S1, and now the control unit 110 may control the video audio playing unit to play a warning message to warn the user to recover a safe driving posture.

Figure 3:
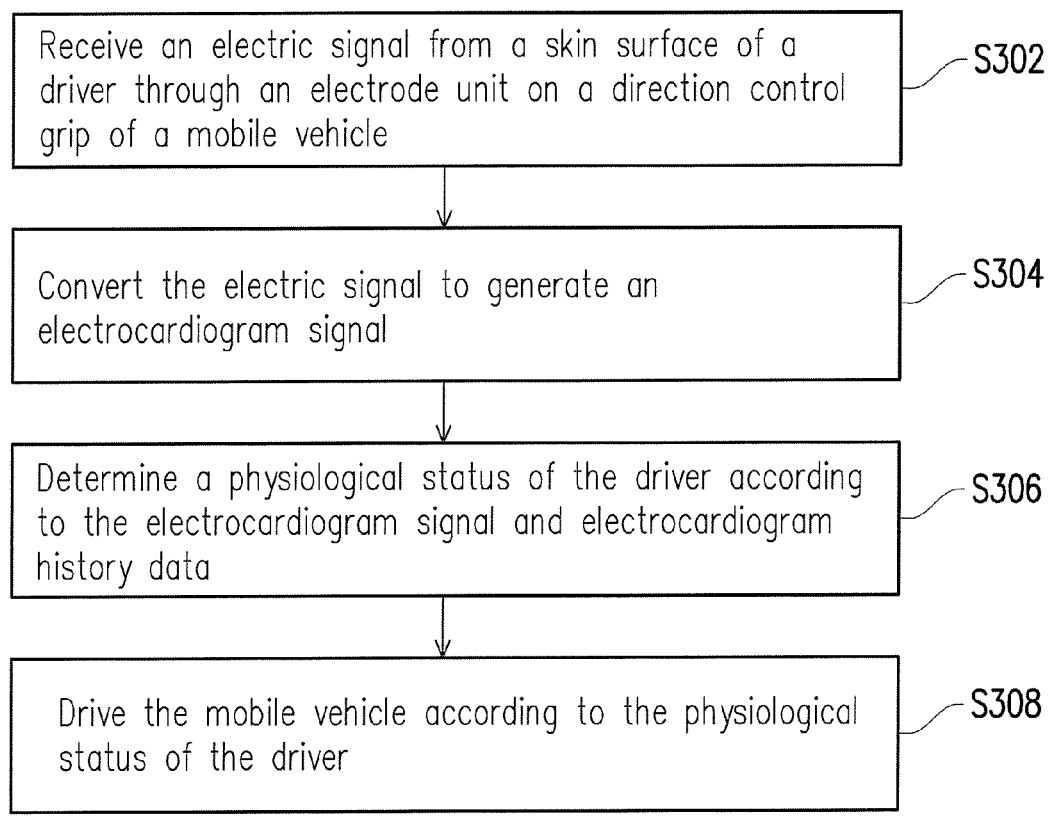
FIG. 3 is a flowchart illustrating a safety monitoring method for a mobile vehicle safety apparatus according to an embodiment of the invention.

FIG. 3 is a flowchart illustrating a safety monitoring method for a mobile vehicle safety apparatus according to an embodiment of the invention. Referring to FIG. 3, according to the above embodiments, it is known that the safety monitoring method for the mobile vehicle safety apparatus may include following steps. First, an electric signal is received from a skin surface of a driver through an electrode unit on a direction control grip of a mobile vehicle (step S302), where the electrode unit may include two electrode patches, though the invention is not limited thereto. Then, the electric signal is converted to generate an electrocardiogram signal (step S304). Then, a physiological status of the driver is determined according to the electrocardiogram signal and electrocardiogram history data (step S306). The electrocardiogram history data is, for example, electrocardiogram signal data of the driver obtained when the driver drives the mobile vehicle last time or before, or electrocardiogram history data can also be electrocardiogram signal data within a predetermined period as the electrode unit starts to receive the electric signals when the driver drives the mobile vehicle for the first time. Finally, the mobile vehicle is driven according to the physiological status of the driver (step S308), for example, it is determined whether to activate the mobile vehicle according to the physiological status of the driver, and the moving speed of the mobile vehicle is adjusted according to the physiological status of the driver.

Figure 4:
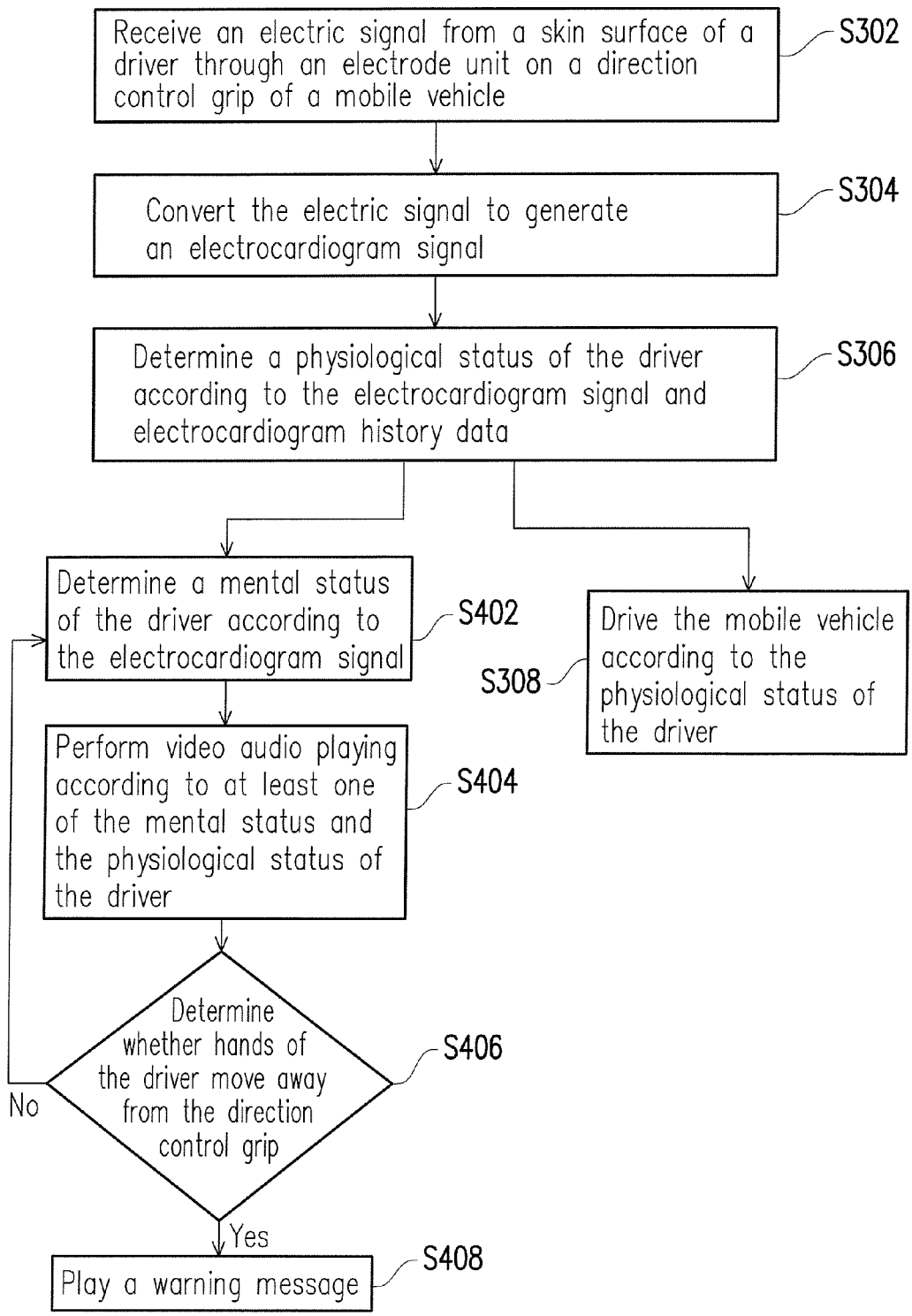
FIG. 4 is a flowchart illustrating a safety monitoring method for a mobile vehicle safety apparatus according to another embodiment of the invention.

FIG. 4 is a flowchart illustrating a safety monitoring method for a mobile vehicle safety apparatus according to another embodiment of the invention. Referring to FIG. 4, in the present embodiment, the safety monitoring method for the mobile vehicle safety apparatus further includes steps S402-S408. After the step S306, a mental status of the driver is also determined according to the electrocardiogram signal (step S402). Then, video audio playing is performed according to at least one of the metal status and the physiological status of the driver (step S404). For example, the predetermined mental status corresponding to the mental status of the driver is determined, and the content of the corresponding video audio database is played according to the predetermined mental status corresponding to the driver. Then, it is determined whether the hands of the driver move away from the direction control grip according to the electrocardiogram signal (step S406), and a warning message is played when the hands of the driver move away from the direction control grip (step S408), so as to warn the driver to recover a normal driving posture. Conversely, if the hands of the driver do not move away from the direction control grip, the flow returns to the step S402.

In summary, in the embodiment of the invention, the physiological status of the driver is determined according to the electrocardiogram signal and the electrocardiogram history data, and the driving unit is controlled to driver the mobile vehicle according to the physiological status of the driver, so as to greatly improve driving safety of the mobile vehicle. In some embodiments, the mental status of the driver can be determined according to the electrocardiogram signal, and video audio playing is performed according to at least one of the mental status and the physiological status of the user, so as to boost or ease the nerve of the driver to make the mental status of the driver to be more suitable for driving the mobile vehicle, and accordingly improve the driving safety of the mobile vehicle.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A mobile vehicle safety apparatus, comprising:
an electrode unit, disposed on a direction control grip of a mobile vehicle, and configured to receive an electric signal from a skin surface of a driver when the driver holds the direction control grip;
an electrocardiogram signal generating unit, coupled to the electrode unit, and converting the electric signal to generate an electrocardiogram signal;
a storage unit, coupled to the electrocardiogram signal generating unit, and storing electrocardiogram history data of the driver;
a driving unit, driving the mobile vehicle to move; and
a control unit, coupled to the electrocardiogram signal generating unit, the storage unit and the driving unit, and determining a physiological status of the driver according to the electrocardiogram signal and the electrocardiogram history data, and controlling the driving unit to drive the mobile vehicle according to the physiological status of the driver; and
a video audio playing unit, coupled to the control unit, wherein the control unit further determines whether hands of the driver move away from the direction control grip according to the electrocardiogram signal, and the control unit controls the video audio playing unit to play a warning message when the hands of the driver move away from the direction control grip.

2. The mobile vehicle safety apparatus as claimed in claim 1, wherein the control unit further determines whether to activate the driving unit according to the physiological status of the driver, and controls the driving unit to adjust a moving speed of the mobile vehicle according to the physiological status of the driver.

3. The mobile vehicle safety apparatus as claimed in claim 1, further comprising:
wherein the control unit further determines a mental status of the driver according to the electrocardiogram signal, and controls the video audio playing unit to perform video audio playing according to at least one of the mental status and the physiological status of the driver.

4. The mobile vehicle safety apparatus as claimed in claim 3, wherein the storage unit further stores a plurality of predetermined video audio databases corresponding to a plurality of predetermined mental statuses, and the control unit controls the video audio playing unit to play content of the corresponding video audio database according to the predetermined mental status corresponding to the driver.

5. A safety monitoring method for a mobile vehicle safety apparatus, comprising:
receiving an electric signal from a skin surface of a driver through an electrode unit on a direction control grip of a mobile vehicle;
converting the electric signal to generate an electrocardiogram signal;
determining a physiological status of the driver according to the electrocardiogram signal and electrocardiogram history data; and driving the mobile vehicle according to the physiological status of the driver;

determining whether hands of the driver move away from the direction control grip; and playing a warning message when the hands of the driver move away from the direction control grip.

6. The safety monitoring method for the mobile vehicle safety apparatus as claimed in claim 5, wherein the step of driving the mobile vehicle according to the physiological status of the driver comprises:

determining whether to activate the mobile vehicle according to the physiological status of the driver, and adjusting a moving speed of the mobile vehicle according to the physiological status of the driver.

7. The safety monitoring method for the mobile vehicle safety apparatus as claimed in claim 5, comprising:

determining a mental status of the driver according to the electrocardiogram signal; and performing video audio playing according to at least one of the mental status and the physiological status of the driver.

8. The safety monitoring method for the mobile vehicle safety apparatus as claimed in claim 7, wherein the step of performing video audio playing according the mental status of the driver comprises:

determining a predetermined mental status corresponding to the mental status of the driver; and playing content of the corresponding video audio database according to the predetermined mental status corresponding to the driver.

\* \* \* \* \*